(12) United States Patent
Rauh et al.

(10) Patent No.: US 9,746,492 B2
(45) Date of Patent: Aug. 29, 2017

(54) PLAUSIBILITY CHECK OF A SENSOR SIGNAL

(71) Applicant: Robert Bosch GmbH, Stuttgart (DE)

(72) Inventors: Christian Rauh, Munich (DE); Christian Korn, Stuttgart (DE); Olaf Koerner, Hamburg (DE); Stephan Rittler, Urbach (DE); Hansjoerg Markus Hild, Plymouth, MI (US)

(73) Assignee: ROBERT BOSCH GMBH, Stuttgart (DE)

(*) Notice: Subject to any disclaimer, the term of this patent is extended or adjusted under 35 U.S.C. 154(b) by 142 days.

(21) Appl. No.: 14/352,094

(22) PCT Filed: Sep. 27, 2012

(86) PCT No.: PCT/EP2012/069046
§ 371 (c)(1),
(2) Date: Apr. 16, 2014

(87) PCT Pub. No.: WO2013/056966
PCT Pub. Date: Apr. 25, 2013

(65) Prior Publication Data
US 2014/0352396 A1    Dec. 4, 2014

(30) Foreign Application Priority Data
Oct. 19, 2011   (DE) .................. 10 2011 084 784

(51) Int. Cl.
*G01D 5/24* (2006.01)
*G05B 23/00* (2006.01)
(Continued)

(52) U.S. Cl.
CPC .......... *G01P 21/00* (2013.01); *G01D 5/24461* (2013.01); *G01N 29/04* (2013.01); *G01N 2291/0289* (2013.01)

(58) Field of Classification Search
CPC ................ G01D 5/24461; G05B 23/0221
(Continued)

(56) References Cited

U.S. PATENT DOCUMENTS 6,023,664 A * 2/2000 Bennet ............... B60R 21/0132
                                                        701/45
6,615,122 B1  9/2003 Yamashita
(Continued)

FOREIGN PATENT DOCUMENTS

CN   1446155 A   10/2003
CN   1447762 A   10/2003
(Continued)

OTHER PUBLICATIONS

International Search Report for PCT/EP2013/069046, dated Jan. 7, 2013.

*Primary Examiner* — David A Rogers
(74) *Attorney, Agent, or Firm* — Norton Rose Fulbright US LLP; Gerard Messina

(57) ABSTRACT

In a method for checking the plausibility of sensor signals, a first sensor element detects at least one first physical quantity and outputs it as a first sensor signal, and a second sensor element detects a second physical quantity correlated with the first physical quantity and outputs it as a second sensor signal. The first sensor element has a first reliability range having an upper limit and/or a lower limit, which range is related to the second physical quantity. The first physical quantity detected by the first sensor element is recognized as plausible if the second physical quantity detected by the second sensor element lies within the corresponding first reliability range of the first sensor element.

15 Claims, 2 Drawing Sheets

(51) Int. Cl.
  *G01P 21/00* (2006.01)
  *G01D 5/244* (2006.01)
  *G01N 29/04* (2006.01)

(58) Field of Classification Search
  USPC .......................................................... 73/1.01
  See application file for complete search history.

(56) References Cited

U.S. PATENT DOCUMENTS

| | | | | |
|---|---|---|---|---|
| 6,693,423 | B2* | 2/2004 | Weser | G01D 5/24461 |
| | | | | 324/207.12 |
| 7,395,178 | B2* | 7/2008 | Hofbauer | G01D 3/08 |
| | | | | 702/150 |
| 7,539,593 | B2 | 5/2009 | Machacek | |
| 8,805,638 | B2* | 8/2014 | Morath | G01D 3/08 |
| | | | | 702/127 |
| 2002/0042694 | A1* | 4/2002 | Henry | G01K 15/00 |
| | | | | 702/188 |
| 2002/0180428 | A1* | 12/2002 | Weser | G01D 5/24461 |
| | | | | 324/207.25 |
| 2005/0246123 | A1* | 11/2005 | Hofbauer | G01D 3/08 |
| | | | | 702/116 |
| 2010/0225500 | A1* | 9/2010 | Ulm | B60R 21/0132 |
| | | | | 340/440 |

FOREIGN PATENT DOCUMENTS

| | | |
|---|---|---|
| DE | 197 04 313 | 8/1998 |
| DE | 10084602 T1 | 4/2002 |
| DE | 101 23 625 | 11/2002 |
| DE | 10 2004 042 467 | 3/2006 |
| EP | 2 289 740 | 3/2011 |
| EP | 2 347 934 | 7/2011 |
| JP | 9-76872 A | 3/1997 |
| JP | 2002-178904 A | 6/2002 |
| WO | 2001070545 A1 | 9/2001 |
| WO | WO 03/042005 | 5/2003 |
| WO | WO 2005/109132 | 11/2005 |

* cited by examiner

PLAUSIBILITY CHECK OF A SENSOR SIGNAL

BACKGROUND OF THE INVENTION

1. Field of the Invention

The present invention is directed to a method for checking the plausibility of sensor signals, and to a device and a method for outputting a trigger signal.

2. Description of the Related Art

Methods and devices known from the related art for checking the plausibility of sensor signals ensure that in the event of a defective sensor element no undesirable behavior occurs in a system, in particular a safety system. Functionalities of the methods and devices are known, which vary depending on the measuring principle and/or type of sensor elements and/or sensor signals and/or the arrangement of the sensor elements. Normally, devices for checking the plausibility of sensor signals include two sensor elements, the plausibility of first sensor signals of a first sensor element being checked, and second sensor signals of a second sensor element being used to check the plausibility of the first sensor signals. If the first sensor signals of the first sensor element are recognized as plausible, then it is assumed that the first sensor element is not defective.

Published German patent application document DE 101 23 625 A1 describes a method and a device for monitoring a measured value acquisition of a physical quantity in which two redundant measured values of a physical quantity are present. In this case a first sensor element detects a first measured value and a second sensor element detects a second measured value. In checking the plausibility, the quotient of the two measured values is formed and is compared with a tolerance range. If a deviation of the quotient from the tolerance range is inadmissible, an error status of a sensor element is then assumed.

Published German patent application document DE 10 2004 042 467 A1 describes a method and a device for generating a trigger signal for a pedestrian safety device, which carry out a trigger and plausibility check of the sensor signals after a collision with an object is detected. In this method a feature extraction is carried out for detecting a pedestrian with the sensor signals which determines the point of impact of the object and a trigger signal for a pedestrian safety device is generated if, during a trigger check, a collision with a pedestrian is detected and the plausibility check of the sensor signals is positive. The device for checking the plausibility of the sensor signals compares the collision-related sensor signals with sensor signals of a central acceleration sensor unit.

BRIEF SUMMARY OF THE INVENTION

In contrast, the method for a plausibility check of sensor signals according to the present invention, and the method for outputting a trigger signal according to the present invention and the device for outputting a trigger signal have the advantage over the related art that at least one first sensor element includes an at least one first reliability range having an upper limit and/or a lower limit. Here, the at least one first reliability range is related to a second physical quantity detected by a second sensor element. An instantaneous value of a first physical quantity detected by the first sensor element is recognized as plausible if an instantaneous value of the second physical quantity detected by the second sensor element lies within the corresponding first reliability range of the first sensor element. The at least one reliability range may be defined, for example, solely by an upper limit or solely by a lower limit, or by both an upper limit and a lower limit.

Specific embodiments of the present invention advantageously allow for a plausibility check via the at least one first reliability range which detects implausible first sensor signals even in the case of properly functioning or non-defective first sensor elements. A first sensor element having a reliability range related to one second physical quantity measures reliable and accurate measured values if the values of the second physical quantity lie within the corresponding reliability range. The measuring accuracy of the first sensor element may be impaired if, for example, the value of the second physical quantity lies outside the at least one first reliability range. In this case, unreliable and/or imprecisely ascertained sensor signals are advantageously not used for a system decision and an associated output of a trigger signal. This may advantageously reduce the number of false trippings of safety systems, in particular of irreversible safety systems such as airbags.

According to a method according to the present invention for checking the plausibility of a sensor signal, in particular of a safety-related sensor signal in a motor vehicle, at least one first physical quantity is detected by one first sensor element and output as the first sensor signal, and one second physical quantity correlated with the first physical quantity is detected by one second sensor element and output as the second sensor signal. According to the present invention, at least the first sensor element has at least one first reliability range having an upper limit and/or a lower limit, which is related to the second physical quantity detected by the second sensor element. An instantaneous value of the first physical quantity detected by the first sensor element is recognized as plausible if an instantaneous value of the second physical quantity detected by the second sensor element lies within the corresponding first reliability range of the first sensor element.

Specific embodiments of a method according to the present invention for outputting a trigger signal, in particular for triggering a safety-related system in a motor vehicle, evaluate one first sensor signal generated by one first sensor element and one second sensor signal generated by one second sensor element. To monitor a triggering criterion, the instantaneous first sensor signal is compared to one first threshold value. According to the present invention, the triggering criterion is met and the trigger signal is output if the instantaneous first sensor signal of the first sensor element exceeds the assigned first threshold value, and if, by using a method for a plausibility check of a sensor signal, at least the first sensor signal of the first sensor element is recognized as plausible. For the plausibility check of a sensor signal at least the first sensor element has one first reliability range having an upper limit and/or a lower limit, which is related to the second physical quantity detected by the second sensor element. An instantaneous value of the first physical quantity detected by the first sensor element is recognized as plausible if an instantaneous value of the second physical quantity detected by the second sensor element lies within the corresponding first reliability range of the first sensor element.

A device according to the present invention for outputting a trigger signal, in particular for triggering a safety-related system in a motor vehicle, includes one first sensor element which detects a first physical quantity and outputs it as the first sensor signal, and one second sensor element which detects one second physical quantity correlated with the first physical quantity and outputs it as the second sensor signal.

For monitoring a triggering criterion for a trigger signal, an evaluation and control unit compares the instantaneous first sensor signal with a first threshold value. According to the present invention, at least the first sensor element has at least one first reliability range having an upper limit and/or a lower limit which is related to the second physical quantity detected by the second sensor element. The evaluation and control unit recognizes an instantaneous value of the first physical quantity detected by the first sensor element as plausible if one instantaneous value of the second physical quantity detected by the second sensor element lies within the corresponding first reliability range of the first sensor element. The triggering criterion is met when the instantaneous first sensor signal of the first sensor element exceeds the assigned first threshold value and at least the first sensor signal of the first sensor is recognized as plausible. The evaluation and control unit outputs a trigger signal when the triggering criterion is met.

For purposes of monitoring the triggering criterion, it is optionally possible, in addition to the instantaneous first sensor signal, to also compare the instantaneous second sensor signal with a second threshold value. In this case, the triggering criterion is met only when the instantaneous first sensor signal of the first sensor element exceeds the assigned first threshold value and the instantaneous second sensor signal of the second sensor element exceeds the assigned second threshold value, and when, by using a method for checking the plausibility of a sensor signal, at least the first sensor signal of the first sensor element is recognized as plausible.

In the present case, a sensor element is understood to mean a component which directly or indirectly detects a physical quantity or a change in a physical quantity and preferably converts it into an electrical sensor signal. This may be accomplished, for example, by receiving sound and/or structure-borne sound waves, and/or by a position change and/or a route change and/or other known methods of detection. The sensor signals may be statically and/or dynamically ascertained. Furthermore, the sensor signals may be ascertained continuously or at one time.

The ascertained sensor signals may be evaluated by an evaluation and control unit which is integrated into the sensor element and/or is situated outside the sensor element, for example, in a sensor unit and/or in a control device. Here, offsets may be subtracted, for example, and other mathematical operations may be carried out for preparing or further processing the ascertained sensor signals. In this way, from a first detected physical quantity, for example, it is possible to calculate an additional physical quantity which is dependent on the first physical quantity such as, for example, velocities, rotational speeds, forces, energies, probabilities of a particular event, etc.

In the present case, the evaluation and control unit may be understood to mean an electrical device such as, for example, a control device which processes and/or evaluates detected sensor signals. The evaluation and control unit may include at least one interface unit which may be designed on a hardware and/or software basis. In a hardware design, the interface units may, for example, be part of a so-called ASIC system which contains a wide variety of the functions of the evaluation and control unit. It is also possible, however, that the interface units are unique integrated circuits or made up at least partly of discrete components. In a software design, the interface units may be software modules present, for example, on a microcontroller next to other software modules. Also advantageous is a computer program product having program code which is stored on a machine-readable medium such as a semiconductor memory, a hard disk memory or an optical memory and is used for the evaluation when the program is executed by the evaluation and control unit.

A plausibility check is understood to mean a method in connection with which a result or a value of an ascertained physical quantity is checked in order to verify whether this value is acceptable and/or perspicuous and/or reproducible and/or plausible. In particular, the arrival of a crash situation is accepted as an event and its plausibility is checked.

It is particularly advantageous that the sensor elements are able to detect the physical quantities using the same measuring principles and/or different measuring principles at the same and/or different points of measurement. Thus, an event may be deduced in a variety of ways. In addition, it is possible to investigate a variety of environmental conditions which restrict the measuring accuracy of the sensor element and to use them for the plausibility check. Thus, measuring errors and/or inaccuracies in measurement results as a result of external influences may advantageously be virtually eliminated. Moreover, additional known plausibility checking methods may be used as assurance without these being negatively influenced. Thus, it is advantageously ensured that exclusively plausible and reliable sensor data are output for further processing and/or for triggering a corresponding safety function.

In one advantageous embodiment of the method for checking the plausibility of sensor signals according to the present invention, it is possible using the two sensor elements to detect accelerations and/or pressures and/or structure-borne sound waves and/or yaw rates. Thus, for example, yaw rate sensors may have a reliability range with respect to the instantaneously effective acceleration. Where an acceleration sensor measures the acceleration at a comparable measurement point, a reliable function of the yaw rate sensor may be advantageously ensured experimentally and/or by design, if the detected instantaneous acceleration values lie within the reliability range of the yaw rate sensor. This makes it possible to use yaw rate sensors in an advantageous manner for crash detection; inaccurate and/or implausible sensor signal values of the yaw rate sensors may be detected due to excessively high acceleration rates. Similarly, values of additional sensor elements may also be checked and used for checking the plausibility of the first sensor signal of the first sensor element during crash detection, if the physical quantities detected by the additional sensor elements is also correlated with the physical quantity detected by the first sensor element.

It is particularly advantageous that for outputting a trigger signal the sensor elements detect crash-related physical quantities. This advantageously guarantees that the sensor units react to an identical event such as, for example, a crash event. In a crash, the detected physical quantities, for example, pressures and/or yaw rates and/or sounds and/or accelerations change as a result of impact. That means that the ascertained measured values are correlated by the shared event and display this event.

In one advantageous embodiment of the method according to the present invention, the trigger signal activates a safety-related system. A safety-related system is reliably activated in an advantageous manner as a result of the reliable crash detection and a premature and/or faulty activation based on inaccurate sensor signals is prevented.

In one advantageous embodiment of the device according to the present invention, the sensor elements detect crash-related physical quantities using the same measuring principles and/or different measuring principles at the same and/or different measuring points. Thus, the device may be used in a variety of ways to deduce an event and above all a crash. Furthermore, a variety of environmental conditions which restrict the measuring accuracy of the sensors may be investigated and used to check the plausibility of the first sensor signal of the first sensor element. Thus, measuring errors and/or inaccuracies in measurement results due to external circumstances may advantageously be virtually eliminated. In particular, it is possible to filter out measurement results whose connection with the external stimulus is unclear as a result of potential distortions by other physical quantities. Moreover, additional known plausibility checking methods may be advantageously used as assurance. In this way it is advantageously ensured that only plausible and reliable sensor data are used for further processing and/or for outputting a trigger signal.

In one further advantageous embodiment of the device, the two sensor elements detect accelerations and/or pressures and or structure-borne sounds and/or yaw rates, for example. A reliable function of the sensor element whose measured values are checked for plausibility may be advantageously ensured experimentally and/or by design. Since accelerations and/or pressures and/or structure-borne sounds and/or yaw rates are physical quantities which are changed in a crash situation and which may influence the measurement result of a sensor element which detects one of the physical quantities, the introduction of a corresponding reliability range for these physical quantities in the sensor element whose plausibility is to be checked, makes it advantageously possible by using these other sensor elements to draw a more accurate conclusion on the reliability of the sensor signals of the sensor element whose plausibility is to be checked when sensing a crash, inaccurate and/or implausible measuring values being able to be detected.

In one further advantageous embodiment of the device according to the present invention, the threshold values and/or the at least one reliability range is/are stored in a memory unit. The stored values may be quickly accessed in an advantageous manner. Furthermore, such a memory unit is normally present in the evaluation and control unit, which is why no additional costs are incurred.

In conjunction with the present invention, a crash is understood to mean not only the collision with another object, such as an obstacle and/or another user of the road, but also a rollover of the vehicle.

Exemplary embodiments of the present invention are represented in the drawing and are explained in greater detail in the following description. In the drawing, the same reference numerals denote components or elements which carry out the same or analog functions.

DETAILED DESCRIPTION OF THE INVENTION

Different methods are known for checking the plausibility of first sensor signals of a first sensor element with second sensor signals of a second sensor element. For example, the first and second sensor signals may be generated by sensor elements using comparable measuring principles and identical measuring points. In this case, the first and second sensor signals are read out cyclically and compared with one another by an evaluation and control unit. In this plausibility check the sensor signals may be compared with one another directly and/or via a quotient and/or via a difference. If, for example, the difference and/or the quotient of the first and second sensor signals exceed(s) a defined limit, the first sensor signals are considered invalid and/or the first sensor element is considered defective.

Likewise, the first and second sensor signals may be generated using comparable measuring principles and different measuring points. In addition, the first and second sensor signals may be generated by sensor elements using non-comparable measuring principles and identical and/or different measuring points. In this plausibility check, the first sensor signals of the first sensor element may not be directly compared with the second sensor signals of the second sensor element. A direct comparison is not practicable due to different measuring points and installation locations such as, for example, inside a control device and outside the control device and/or due to differing directions of detection such as, for example, in the direction of travel and transverse to the direction of travel, and/or due to non-comparable measuring principles in which, for example, different physical quantities are detected. In such a plausibility checking method it is checked, for example, whether the first sensor signals exceed a predefined first threshold value and whether the second sensor signals exceed a predefined second threshold value. If this is the case with the two sensor signals, then the first sensor element whose plausibility is to be checked is considered to be functional and the first sensor signals are considered valid.

Figure 1:
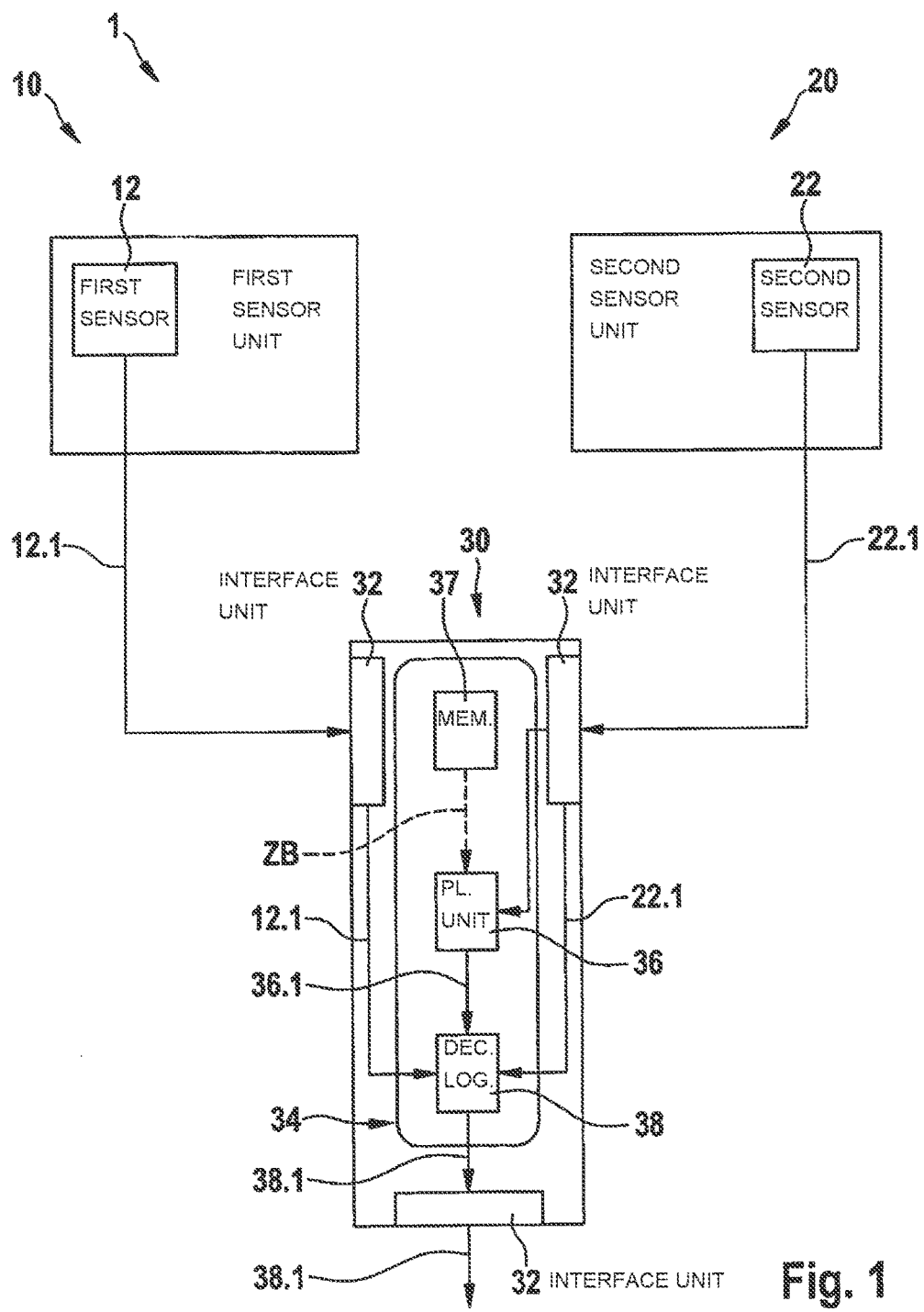
FIG. 1 shows a schematic block diagram of one exemplary embodiment of a device according to the present invention for outputting a trigger signal.

As is apparent from FIG. 1, the depicted exemplary embodiment of a device 1 according to the present invention for generating a trigger signal 38.1 includes a first sensor unit 10 having a first sensor element 12 which detects a first physical quantity and outputs it as first sensor signal 12.1, and a second sensor unit 20 having a second sensor element 22 which detects a second physical quantity correlated with the first physical quantity and outputs it as second sensor signal 22.1. To monitor a triggering criterion for a trigger signal 38.1, an evaluation and control unit 30 compares at least the instantaneous first sensor signal 12.1 with a first threshold value.

Evaluation and control unit 30 depicted in the exemplary embodiment includes three interface units 32 and a processing unit 34. Processing unit 34 includes a memory unit 37, a plausibility checking unit 36 and a decision logic 38. Evaluation and control unit 30 receives first sensor signals 12.1 of first sensor element 12 and second sensor signals 22.1 of second sensor 22 via at least one interface unit 32 and evaluates received signals 12.1, 22.1 in processing unit 34. The evaluation may be used, for example, to subtract offsets present and/or determine mean values and/or increase the signal strength through multiplication by a factor. Alternatively, the evaluation may also be carried out in first sensor unit 10 and/or in second sensor unit 20. Corresponding evaluation units may be arranged in sensor units 10, 20 for this purpose.

According to the present invention, at least first sensor element 12 has at least one first reliability range RR having an upper limit and/or a lower limit. The at least one reliability range RR relates to the second physical quantity detected by second sensor element 22. Plausibility checking unit 36 of evaluation and control unit 30 recognizes an instantaneous value of the first physical quantity detected by first sensor element 12 as plausible if an instantaneous value of the second physical quantity detected by second sensor element 22 lies within corresponding first reliability range RR of first sensor element 12. In the depicted exemplary embodiment sensor elements 12, 22 detect crash-related physical quantities using the same measuring principles and/or using different measuring principles at the same and/or at different measuring points. In particular, sensor elements 12, 22 may detect the same physical quantities differently and/or detect different physical quantities in the same or different value ranges. For example, sensor elements 12, 22 may detect the same physical quantities, the resolution of one of sensor elements 12, 22 being more precise and/or one of sensor elements 12, 22 having a greater value range and/or sensor elements 12, 22 detecting the same physical quantities at different measuring points. The two sensor elements 12, 22 may, for example, detect accelerations and/or pressures and/or structure-borne sound and/or yaw rates.

In the depicted exemplary embodiment the measured values of one yaw rate sensor 12 may be recognized as plausible with the aid of an acceleration sensor 22, since the instantaneous acceleration influences the accuracy of the measuring result of yaw rate sensor 12. In a further variant the values of a yaw rate sensor 12 may alternatively or in addition be recognized as plausible with the aid of a structure-borne sound sensor. To obtain a faster evaluation, the threshold values and/or the at least one reliability range RR is/are stored in memory unit 37.

Decision logic 38 of evaluation and control unit 30 checks whether the triggering criterion is met. The triggering criterion is met if at least instantaneous first sensor signal 12.1 of first sensor element 12 exceeds the assigned first threshold value and at least first sensor signal 12.1 of first sensor 12 is recognized as plausible. Evaluation and control unit 30 outputs trigger signal 38.1 via an interface unit 32 if the triggering criterion is met. To check the triggering criterion, plausibility checking unit 36 outputs a plausibility check signal 36.1 to decision logic 38. Here, plausibility check signal 36.1 reveals whether the value of the first physical quantity is plausible or not.

For purposes of monitoring the triggering criterion, evaluation and control unit 30 may optionally, in addition to the instantaneous first sensor signal 12.1, also compare the instantaneous second sensor signal 22.1 with a second threshold value. In this case, the triggering criterion is met only if instantaneous first sensor signal 12.1 of first sensor element 12 exceeds the assigned first threshold value and instantaneous second sensor signal 22.1 of second sensor element 22 exceeds the assigned second threshold value, and if at least first sensor signal 12.1 of first sensor element 12 is recognized as plausible.

Figure 2:
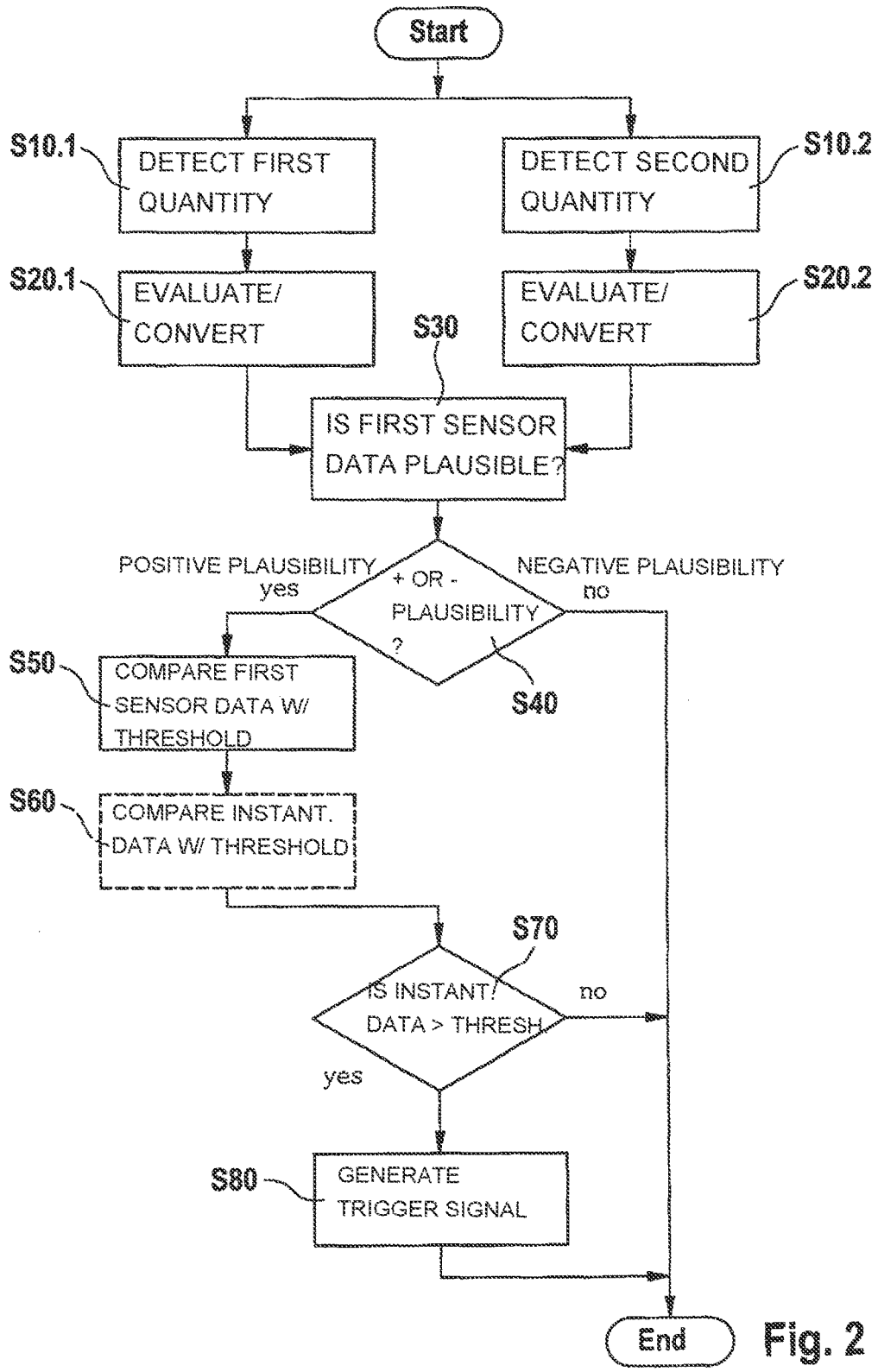
FIG. 2 shows a schematic block diagram of one exemplary embodiment of a method according to the present invention for checking the plausibility of sensor signals and for outputting a trigger signal.

As is apparent from FIG. 2, at least one first physical quantity is detected by one first sensor element 12 in a method step S10.1 and output as first sensor signal 12.1. In a method step S10.2, one second physical quantity correlated with the first physical quantity is detected by one second sensor element 22 and output as second sensor signal 22.1. In this case, the measured physical quantities result from the same event, such as a crash, for example. This means that correlated crash-related physical quantities are detected. The timing of the detection of the two physical quantities may be in parallel, i.e., simultaneous, or offset. Furthermore, the same physical quantities and/or different physical quantities may be detected using the same measuring principles and/or using different measuring principles at the same and/or at difference measuring points in the same and/or different value ranges.

In a method step S20.1, detected first sensor signals 12.1, and in a method step S20.2, second sensor signals 22.1 are evaluated by an evaluation and control unit 30 and/or converted into suitable quantities. This may include, for example, subtraction of an offset and/or the mathematical calculation of correlated physical quantities.

According to the present invention, at least first sensor element 12 has at least one first reliability range RR having an upper limit and/or a lower limit which is related to the second physical quantity detected by second sensor element 22. In this case, the second physical quantity influences the measurement result of the physical quantity detected by first sensor element 12. In step S30 it is checked whether sensor signal 12.1 output from first sensor element 12 is plausible. First sensor signal 12.1 of first sensor element 12 is accurate and/or reliable or plausible as long as the values of the second physical quantity detected by second sensor element 22 lie within reliability range RR of first sensor element 12. For this reason, one instantaneous value of the first physical quantity detected by first sensor element 12 is recognized as plausible in method step S30 if one instantaneous value of the second physical quantity detected by second sensor element 22 lies within first reliability range RR of first sensor element 12. If this is met, then in step S30 corresponding positive plausibility check signal 36.1 is output from plausibility checking unit 36 of evaluation and control unit 30 to decision logic 38 of evaluation and control unit 30 so that decision logic 38 may generate and output corresponding trigger signal 38.1 if further conditions are met. If this is not met, then in step S30 corresponding negative plausibility check signal 36.1 is output from plausibility checking unit 36 of evaluation and control unit 30 to decision logic 38 of evaluation and control unit 30 so that decision logic 38 does not generate or output any trigger signal 38.1, irrespective of other conditions.

As is also apparent from FIG. 2, a method according to the present invention for outputting a trigger signal 38.1 includes the above described method steps S10.1 through S30 and a further plausibility check. For that reason, in step S40 it is checked whether plausibility checking unit 36 of evaluation and control unit 30 outputs a positive or negative plausibility check signal 36.1 to decision logic 38 of evaluation and control unit 30. If in step S40 negative plausibility check signal 36.1 is recognized, then the method for outputting a trigger signal 38.1 is terminated. If in step S40 the positive plausibility check signal 36.1 is recognized, then in step 50 the instantaneous value of the detected first physical quantity or first sensor signal 12.1 is compared with a predefined first threshold value. In method step S70 it is then checked whether the instantaneous value of the detected first physical quantity or of first sensor signal 12.1 exceeds the first threshold value. If the instantaneous value of the detected physical quantity or of first sensor signal 12.1 exceeds the corresponding threshold value, then in step S80 the trigger signal 38.1 is generated and output. Trigger signal 38.1 activates, for example, a safety-related occupant safety system, such as an airbag and/or a roll-bar and/or a seat belt tightener.

If the instantaneous value of the detected physical quantity or of first sensor signal 12.1 does not exceed the corresponding threshold value, then the method is terminated and no trigger signal 38.1 is output.

Thus, the method according to the present invention for outputting a trigger signal 38.1 checks whether the event sensed by sensor elements 12, 22 is plausible or not. The event in the depicted exemplary embodiment is a crash or a vehicle rollover which is recognized as plausible if ascertained first sensor signal 12.1 exceeds an assigned first threshold value and is recognized as plausible. The monitored triggering criterion is met if the instantaneous value of first sensor signal 12.1 exceeds the assigned threshold value and if at least first sensor signal 12.1 of first sensor 12 is recognized as plausible by the above described method for checking the plausibility of a sensor signal in steps S10.1 through S30.

Optionally, in step S60 represented by dashed lines, the instantaneous value of the detected second physical quantity or of second sensor signal 22.1 may also be compared with a predefined second threshold value. The two steps S50 and S60 may be carried out in parallel, i.e., simultaneously or offset to one another. In this case, it is then checked in method step S70 whether the instantaneous value of the detected first physical quantity or of first sensor signal 12.1 exceeds the first threshold value, and the instantaneous value of the second detected physical quantity or of second sensor signal 22.1 exceeds the second threshold value. If both instantaneous values of the detected physical quantities or of both sensor signals 12.1, 22.1 exceed the respective corresponding threshold, then in step S80 trigger signal 38.1 is generated and output.

If in this exemplary embodiment at least one of the two instantaneous values of the detected physical quantities or of sensor signals 12.1, 22.1 does not exceed the corresponding threshold value, then the method is terminated and no trigger signal 38.1 is output.

Thus, in this exemplary embodiment the method according to the present invention for outputting a trigger signal 38.1 checks whether the event sensed by sensor elements 12, 22 is plausible or not. The event in the exemplary embodiment depicted is a crash or a vehicle rollover which is recognized as plausible if the ascertained sensor signals 12.1, 22.1 each exceed a threshold value assigned to it and at least first sensor signal 12.1 is plausible. The monitored triggering criterion is met if the instantaneous value of first sensor signal 12.1 and the instantaneous value of second sensor signal 22.2 each exceed the threshold value assigned to it and if at least first sensor signal 12.1 of first sensor 12 is recognized as plausible in steps S10.1 through S30 by the above-described method for checking the plausibility of a sensor signal.

In an alternative exemplary embodiment not shown it is possible to first check whether the instantaneous value of the first detected physical quantity or of the first sensor signal exceeds the first threshold value and whether the instantaneous value of the detected second physical quantity or of the second sensor signal exceeds the second threshold value, before it is checked whether at least the first sensor signal is plausible. Alternatively, these checks may be carried out in parallel or simultaneously.

It is likewise possible that a third sensor element not shown checks the plausibility of first sensor signals 12.1 of first sensor element 12 and/or second sensor signals 22.1 of second sensor element 22. Here, first sensor element 12 and second sensor element 22 each have a reliability range RR related to a physical quantity which is detected by the third sensor element and converted into third sensor signals.

What is claimed is:

1. A method for generating a trigger signal, comprising:
   generating, by a first sensor element, a first sensor signal;
   generating, by a second sensor element, a second sensor signal;
   comparing the first sensor signal with a first threshold value;
   comparing the second sensor signal with a second threshold value;
   determining a triggering criterion has been met when (i) the first sensor signal exceeds the first threshold value and (ii) the first sensor signal is recognized as plausible; and
   outputting a trigger signal when the triggering criterion has been met;
   wherein the plausibility of a sensor signal is checked by performing the following:
      detecting, by the first sensor element, at least one first physical quantity, wherein the at least one first physical quantity is output by the first sensor element as the first sensor signal;
      detecting, by the second sensor element, a second physical quantity correlated with the first physical quantity, wherein the second physical quantity is output by the second sensor element as the second sensor signal, and wherein at least the first sensor element has at least one first reliability range having at least one of an upper limit and a lower limit, the at least one first reliability range being related to the second physical quantity detected by the second sensor element; and
      determining an instantaneous value of the first physical quantity detected by the first sensor element as being plausible if an instantaneous value of the second physical quantity detected by the second sensor element at a correspondent instant lies within the at least one first reliability range of the first sensor element;
   wherein the plausibility check, which is performed based on the at least one first reliability range, detects implausible first sensor signals even if the first sensor element functions properly or is non-defective.

2. The method as recited in claim 1, wherein the first and second sensor elements detect crash-related physical quantities.

3. The method as recited in claim 2, wherein the trigger signal activates a safety-related system.

4. The method as recited in claim 1, further comprising: outputting a trigger signal if the sensor signal is plausible.

5. The method as recited in claim 4, wherein the first and second sensor elements detect the first and second physical quantities in the same or different value ranges, the first and second physical quantities being different types of physical quantities.

6. The method as recited in claim 1, wherein the first and second sensor elements detect the first and second physical quantities in the same or different value ranges, the first and second physical quantities being different types of physical quantities.

7. A device for generating a trigger signal, comprising:
   a first sensor element detecting a first physical quantity and outputting a first sensor signal corresponding to the first physical quantity, wherein at least the first sensor element has at least one first reliability range having at least one of an upper limit and a lower limit;
   a second sensor element detecting a second physical quantity correlated with the first physical quantity and outputting a second sensor signal corresponding to the second physical quantity, wherein the at least one first reliability range of the first sensor element is related to the second physical quantity detected by the second sensor element; and an evaluation and control unit configured to:
  (i) determine an instantaneous value of the first physical quantity detected by the first sensor element as being plausible if an instantaneous value of the second physical quantity detected by the second sensor element at a correspondent instant lies within the at least one first reliability range of the first sensor element;
  (ii) determine a triggering criterion has been met when the first sensor signal exceeds a first threshold value and the first physical quantity corresponding to the first sensor signal is determined as plausible; and
  (iii) output a trigger signal when the triggering criterion has been met;
wherein the plausibility check, which is performed based on the at least one first reliability range, detects implausible first sensor signals even if the first sensor element functions properly or is non-defective.

8. The device as recited in claim 7, wherein the first and second sensor elements detect crash-related physical quantities at different measuring points.

9. The device as recited in claim 8, wherein the first and second sensor elements detect at least one of an acceleration, a pressure, a structure-borne sound, and a yaw rate.

10. The device as recited in claim 8, wherein at least one of the first threshold value and the at least one reliability range is stored in a memory unit.

11. The device as recited in claim 7, wherein the first and second sensor elements detect the first and second physical quantities in the same or different value ranges, the first and second physical quantities being different types of physical quantities.

12. A method for generating a trigger signal, comprising:
generating, by a first sensor element, a first sensor signal;
generating, by a second sensor element, a second sensor signal;
comparing the first sensor signal with a first threshold value;
comparing the second sensor signal with a second threshold value;
determining a triggering criterion has been met when (i) the first sensor signal exceeds the first threshold value and (ii) the first sensor signal is recognized as plausible; and
outputting a trigger signal when the triggering criterion has been met;
wherein the plausibility of a sensor signal is checked by performing the following:
  detecting, by the first sensor element, at least one first physical quantity, wherein the at least one first physical quantity is output by the first sensor element as the first sensor signal;
  detecting, by the second sensor element, a second physical quantity correlated with the first physical quantity, wherein the second physical quantity is output by the second sensor element as the second sensor signal, and wherein at least the first sensor element has at least one first reliability range having at least one of an upper limit and a lower limit, the at least one first reliability range being related to the second physical quantity detected by the second sensor element; and
  determining an instantaneous value of the first physical quantity detected by the first sensor element as being plausible if an instantaneous value of the second physical quantity detected by the second sensor element at a correspondent instant lies within the at least one first reliability range of the first sensor element;
wherein the first and second sensor elements detect the first and second physical quantities using different measuring principles.

13. The method as recited in claim 12, wherein the first and second sensor elements detect crash-related physical quantities.

14. The method as recited in claim 13, wherein the trigger signal activates a safety-related system.

15. A device for generating a trigger signal, comprising:
a first sensor element detecting a first physical quantity and outputting a first sensor signal corresponding to the first physical quantity, wherein at least the first sensor element has at least one first reliability range having at least one of an upper limit and a lower limit;
a second sensor element detecting a second physical quantity correlated with the first physical quantity and outputting a second sensor signal corresponding to the second physical quantity, wherein the at least one first reliability range of the first sensor element is related to the second physical quantity detected by the second sensor element; and
an evaluation and control unit configured to:
  (i) determine an instantaneous value of the first physical quantity detected by the first sensor element as being plausible if an instantaneous value of the second physical quantity detected by the second sensor element at a correspondent instant lies within the at least one first reliability range of the first sensor element;
  (ii) determine a triggering criterion has been met when the first sensor signal exceeds a first threshold value and the first physical quantity corresponding to the first sensor signal is determined as plausible; and
  (iii) output a trigger signal when the triggering criterion has been met;
wherein the first and second sensor elements detect the first and second physical quantities using different measuring principles.

* * * * *